United States Patent
Dhanjal et al.

(10) Patent No.: US 10,166,686 B1
(45) Date of Patent: Jan. 1, 2019

(54) PORTABLE, SELF-CONTAINED, READY-TO-USE, STERILE ENCLOSURE FOR FILLING STERILE PRODUCTS

(71) Applicants: Jasbir Dhanjal, Trabuco Canyon, CA (US); Kirk McMullin, Villa Park, CA (US)

(72) Inventors: Jasbir Dhanjal, Trabuco Canyon, CA (US); Kirk McMullin, Villa Park, CA (US)

( * ) Notice: Subject to any disclaimer, the term of this patent is extended or adjusted under 35 U.S.C. 154(b) by 0 days.

(21) Appl. No.: 15/732,595

(22) Filed: Nov. 30, 2017

(51) Int. Cl.
| | |
|---|---|
| *B65B 3/00* | (2006.01) |
| *B25J 21/02* | (2006.01) |
| *B65B 31/02* | (2006.01) |
| *B65B 55/02* | (2006.01) |
| *A61M 5/178* | (2006.01) |
| *B67C 3/02* | (2006.01) |
| *A61J 1/14* | (2006.01) |
| *B67C 7/00* | (2006.01) |
| *A61J 1/03* | (2006.01) |

(52) U.S. Cl.
CPC ............ *B25J 21/02* (2013.01); *A61M 5/1782* (2013.01); *B65B 3/003* (2013.01); *B65B 31/02* (2013.01); *B65B 55/027* (2013.01); *A61J 1/03* (2013.01); *A61J 1/14* (2013.01); *B65B 2210/06* (2013.01); *B67C 3/02* (2013.01); *B67C 7/0073* (2013.01)

(58) Field of Classification Search
CPC .......... B25J 21/00; B25J 21/005; B25J 21/02; B65B 31/02; B65B 31/025; B65B 31/027; B65B 31/028; B65B 55/025; B65B 55/027; B65B 2210/06; B65B 2210/08; B65B 3/003; B67C 7/0073; B67C 7/008; B67C 7/0086; B67C 3/2642; A61L 2202/23; A61J 1/1443; A61J 1/145; A61J 1/1456; A61J 1/18; A61M 5/1782
USPC .................................................. 312/1; 53/86
See application file for complete search history.

(56) References Cited

U.S. PATENT DOCUMENTS

| | | | | |
|---|---|---|---|---|
| 2,786,740 A | * | 3/1957 | Taylor | B25J 21/02 312/1 |
| 5,007,232 A | * | 4/1991 | Caudill | B65B 55/10 141/63 |
| 6,235,072 B1 | * | 5/2001 | Kopylov | B01D 46/0023 55/338 |
| 8,298,054 B2 | * | 10/2012 | Hodge | G05B 15/02 454/187 |

(Continued)

FOREIGN PATENT DOCUMENTS

DE   102012005683   *   9/2013   ............... B01L 1/02

*Primary Examiner* — Stephen F. Gerrity
*Assistant Examiner* — Joshua G Kotis (57) ABSTRACT

A portable, self-contained, ready-to-use, sterile enclosure used in the filling of small quantities of sterile products. Particularly, an enclosure that contains the vials or bottles to be filled, as well as all necessary fittings and filters integrated with the assembled apparatus, and which as a total assembly can be reduced to a small package size, thereby enabling the entire assembly to be sterilized remotely in one step by gamma irradiation or ethylene oxide gas. The design of the enclosure assembly further enables shipment to the end user in sterile ready-to-use condition, and allows the end user to perform sterile filling within the enclosure without the need for any aseptic connections or further equipment sterilization steps.

14 Claims, 4 Drawing Sheets

(56) References Cited

U.S. PATENT DOCUMENTS

| | | | | |
|---|---|---|---|---|
| 8,337,751 B2* | 12/2012 | Stewart | .................. | A47K 3/286 |
| | | | | 135/94 |
| 2009/0223592 A1* | 9/2009 | Procyshyn | ............... | B25J 21/00 |
| | | | | 141/2 |
| 2011/0258837 A1* | 10/2011 | Scannon | ............ | G05B 19/4188 |
| | | | | 29/592 |
| 2012/0031042 A1* | 2/2012 | Zambaux | .................. | B25J 21/02 |
| | | | | 53/167 |
| 2013/0017131 A1* | 1/2013 | Galliher | ................ | C12M 37/00 |
| | | | | 422/544 |
| 2014/0366486 A1* | 12/2014 | Hinz | .................. | A61M 5/1782 |
| | | | | 53/428 |
| 2015/0107190 A1* | 4/2015 | Zambaux | ................. | B25J 21/02 |
| | | | | 53/287 |
| 2018/0037343 A1* | 2/2018 | Procyshyn | .......... | A61M 5/1782 |

* cited by examiner

PORTABLE, SELF-CONTAINED, READY-TO-USE, STERILE ENCLOSURE FOR FILLING STERILE PRODUCTS

BACKGROUND

In the pharmaceutical industry, there has long been a need to fill sterile drug products, such as solutions, suspensions, gels, ointments, and powders into sterile containers, such as vials, pre-filled syringes, plastic eye-drop bottles, or IV bags.

In some instances, sterility of the drug product has been achieved by first filling the drug into vials or bottles, and then sterilizing the filled containers by exposure to steam, such as in an autoclave, or by exposing the product to sterilizing doses of radiation. However, in many cases, the product, by it's nature, may be damaged by exposure to extreme heat or radiation and therefore cannot be sterilized by these methods. In these circumstances, sterility may be achieved by the process of sterilizing the drug product and the vials or bottles separately, and by then filling the sterile drug product into the sterile containers in a cleanroom environment, also known as an aseptic environment. The process of filling sterile product in an aseptic environment is often termed an aseptic filling operation.

Historically, there are several types of cleanrooms, or aseptic environments that have been used for the filling of sterile drug products. One type accommodates human operators working directly in the filling room. In these traditional cleanrooms, an aseptic environment is achieved through the combination of the constant circulation of sterile-filtered air, the maintenance of higher air pressure in the filling room than in the adjacent rooms, the periodic sanitization of the room and the filling equipment within the room, the sterilization of the drug product and the containers prior to entry into the room, and the gowning of the people working in the room with sterile outer garments.

Another type of environment that is often used for filling small quantities of sterile drug product is the laminar flow workbench, or laminar flow hood. A laminar flow workbench provides a localized aseptic environment through the continuous flow of sterile air. When small quantities of sterile containers are to be filled, such as in certain research settings, or in some compounding pharmacies, it has been known for a technician, wearing sterile gloves and gown, to introduce a bag of pre-sterilized containers onto the surface of the laminar flow workbench, and to then fill pre-sterilized drug product into the sterile containers, and to subsequently stopper, cap or seal the containers in the aseptic environment of the laminar flow air.

Another type of environment for aseptic filling is an isolator with glove-box fittings. In an isolator human operators do not physically enter the enclosure. Rather, they are able to perform manipulations from outside the enclosure by reaching into the isolator with the use of integral sterile gloves or integral isolator suits, which provide a barrier between the person performing the manipulation and the sterile environment inside the isolator. The isolator is decontaminated with an antimicrobial gas or vapor, often the gas being vaporized hydrogen peroxide. Sterility of the environment is maintained by keeping the isolator closed and by circulating sterile-filtered air through the isolator. The empty containers to be filled are normally sterilized externally to the isolator and are then introduced into the isolator through a docking port, or rapid transfer port, that allows for sterile transfer from one sterile enclosure into another.

Issues with Current Designs when Applied to Sterile Filling Small Numbers of Containers:

In the current state of the art, there are problems or issues associated with each type of aseptic filling environment referenced, most particularly as they apply to the filling of small quantities of sterile product. Specific issues are capital equipment costs, high operating costs, space utilization, labor requirements, sterility assurance levels, and lack of portability.

Traditional aseptic cleanrooms and large-scale isolators are expensive to build or purchase and are also costly to maintain. Once built and qualified, the cleanrooms must be constantly maintained under aseptic conditions. This results in high costs for utilities, personnel and materials. Cleanrooms and isolators also require extensive supporting infrastructure to maintain and operate, including air circulators, air filters, maintenance and validation of decontamination equipment, and calibration programs for monitoring equipment. Further, each of these systems for aseptic filling requires extensive time and labor to set up and prepare for each sterile fill.

When filling large quantities of sterile containers, the costs and effort associated with large cleanrooms or large isolators and their associated machinery may be justified. However, when filling small quantities of product, such as is common in small clinical trials, in research settings, in compounding pharmacies, or in the manufacture of customized made-to-order medications, the use of large scale filling machines inside of cleanrooms or the use of fixed-in-place isolators are often not practical.

Another issue with traditional cleanrooms or fixed-in-place isolators is the size of the space required to house the equipment. Even a small cleanroom or isolator may require 400 square feet (or greater) of facility space. Larger cleanrooms and isolators will require as much as 2000 square feet of facility space to operate and maintain. These high space requirements apply not only when the cleanroom or isolator is in use, but also when not in use.

Yet another issue with the current state of the art is that traditional cleanroom environments and the laminar flow workbench aseptic filling environments often do not demonstrate the ideal level of sterility assurance. Bacteria are often found in these environments, due to the human presence within the workspace, and also due to the inability to fully sterilize all surfaces and equipment within the room or workbench. One of the standard measures for contamination in a cleanroom is the use of a sterile media fill, in which a number of bottles are aseptically filled with microbiological growth media, and are then examined after incubation for signs of bacterial or fungal growth. It is well known that, because of the design of these environments, as well as the presence of humans in the workspace, the level of sterility assurance obtained by performing aseptic filling in these environments is significantly lower than that achieved with terminal sterilization methods, such as is achieved with an autoclave. Because of the higher risk of bacterial or fungal contamination in these environments, governmental regulatory authorities have determined that aseptic filling in these environments should only be used as a last resort, when it can be demonstrated that the final filled product cannot be terminally sterilized, by use of a method such as sterilization in a steam autoclave, or by gamma irradiation.

While isolators can provide greater sterility assurance than aseptic filling rooms, one problem with using isolators is the difficulty in assuring that the vapor hydrogen peroxide disinfectant is exposed to all surfaces within the isolator. Other problems are the time required for removal of the vapor hydrogen peroxide gas from the isolator, and the high cost of purchasing and maintaining fixed-in-place isolators.

Another issue with the current state of the art is that the existing systems for aseptic filling all require sterilization or decontamination at the site of use, and are not designed for practical transport to distant locations for immediate use. There are various potential uses for a portable, transportable, ready-to-use sterile aseptic filling environment, especially when the number of vials or bottles to be filled are relatively few or are filled infrequently. These include the occasional needs of academic research facilities, small start-up pharmaceutical companies with a need to make sterile product for research purposes, compounding pharmacies for customized medications, and remote internationally located temporary medical facilities. At present, these types of end users, for reasons of cost or logistics, either need to have their product filled by a contract supplier, or they need to use equipment and systems which may not provide the highest level of sterility assurance (such as laminar flow workbenches). The invention and associated method presented here solve this problem for those who need to fill small quantities of sterile product on a periodic basis with a high degree of sterility assurance.

While various technologies and methods are available for high-volume, high cost, sterile filling, there are currently limited options for small-volume non-routine sterile filling.

Often it is impractical or prohibitively expensive to fill just a few containers in an industrial sized clean room or industrial sized isolator. Also, many of those who desire or need to fill a small number of vials of sterile product do not have ready access to fixed-in-place isolators or the associated vapor hydrogen peroxide decontamination equipment.

Advantages

The apparatus taught here addresses or solves many of the issues associated with current aseptic filling rooms, laminar flow workbenches, or sterile filling isolators. The advantages discussed below are especially applicable when the objective is to fill a relatively small number of containers, as opposed to large-scale, high-volume manufacturing operations. For example, the design of the portable, self-contained, sterile enclosure taught here, and the associated method of use thereof, provides much higher sterility assurance levels than that seen with standard cleanrooms or laminar flow workbenches. This is due to the enclosure being completely sealed from the ingress of microorganisms, and is also due the ability to sterilize, in a single sterilization step, the entire system, including the bottles or vials to be filled, using gamma irradiation or ethylene oxide gas. Since all of the components are included with the enclosure assembly at the time of sterilization, there is not any human contact with any materials inside of the enclosure after it is sterilized, and there is no need to make any aseptic connections for introduction of sterile materials into the enclosure.

Also the invention described here is highly portable, does not require sophisticated infrastructure to use, and can be shipped globally, including to remote locations, pre-sterilized and ready to use, at relatively low cost. Furthermore the invention described here can be stored for extensive periods of time, potentially up to several years, in sterile state, ready for immediate use, when needed, without the need for extensive set-up or preparation prior to use. Also, because the enclosure is disposable, there is no need for ongoing infrastructure or space allocation to support use of the apparatus.

The invention taught here addresses the need to fill small numbers of sterile products. By including vials, bottles, prefilled syringes, or other containers inside the enclosure, and as a benefit of the small size of the apparatus when prepared for shipping, it is possible to gamma irradiate, or ethylene oxide gas sterilize the entire enclosure off-site at a contracted facility and to then ship the isolator to the site where the sterile fill will take place. The final filling location could be a research facility, a small drug company, a compounding pharmacy, or a remotely located international medical aid or emergency relief facility. Further, due to it's small size, portability, disposability, and ready-to-use attributes, we can envision the use of this invention to enable the sterile filling of solutions in a space station or space-based laboratory environment.

As a benefit from the low amount of required infrastructure to operate the portable, self-contained enclosure taught here, one can perform a sterile fill with only the enclosure apparatus and a small air blower, such as is commonly used to inflate air mattresses. Further, as a benefit of the fact that the enclosure is completely sealed to the outside environment, one can perform the sterile fill in an uncontrolled environment, without compromising the sterility of the product being filled. As an example, an enclosure assembly constructed according to Embodiment 1 (described below) was gamma irradiated and an experimental sterile fill was performed in an uncontrolled warehouse-like environment, in which the doors to the space were open to the outside. Despite these conditions, the sterile fill of filtered media surprisingly resulted in filled vials and bottles showing no growth upon incubation, thus demonstrating their sterility.

SUMMARY

A portable, self-contained, sterile enclosure used for filling small quantities of sterile products. The apparatus is pre-assembled in entirety, including the vials or bottles to be filled, a filling tool, and also including attached tubing, filters, and gloves. Also included inside the enclosure are means for microbiological testing of the enclosure environment. The enclosure is of a size that is easily shipped and easily sterilized by gamma irradiation or ethylene oxide. By designing the enclosure to be relatively small, and for the purpose of filling a relatively small number of vials or bottles, and by placing the vials inside of the enclosure during initial assembly, it becomes uniquely possible to gamma sterilize the entire assembly, including the enclosed vials in one sterilization step. Also, by specifying a small size, it becomes possible to ship the sterile enclosure ready-to-use for sterile filling. Importantly and uniquely, because the containers are placed inside of the enclosure prior to sterilization, and because the liquid and air sterilization filters or other sterile connectors are included in the assembly at the time of sterilization, the invention is, when delivered to the end user, self-contained and does not require the application of any further sterilization of equipment external to the apparatus prior to use.

Figure 1:
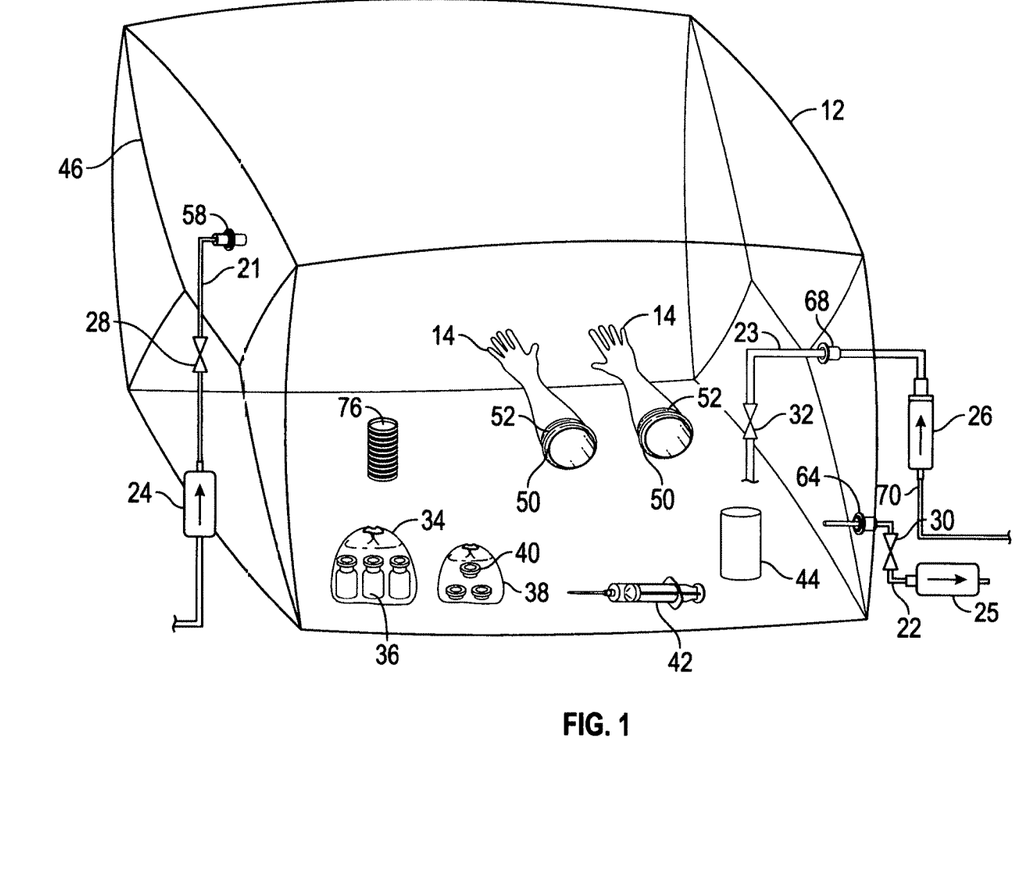
FIG. 1 shows one embodiment of an inflated enclosure assembly that is fully assembled and is ready to be deflated and packaged for sterilization
Figure 2:
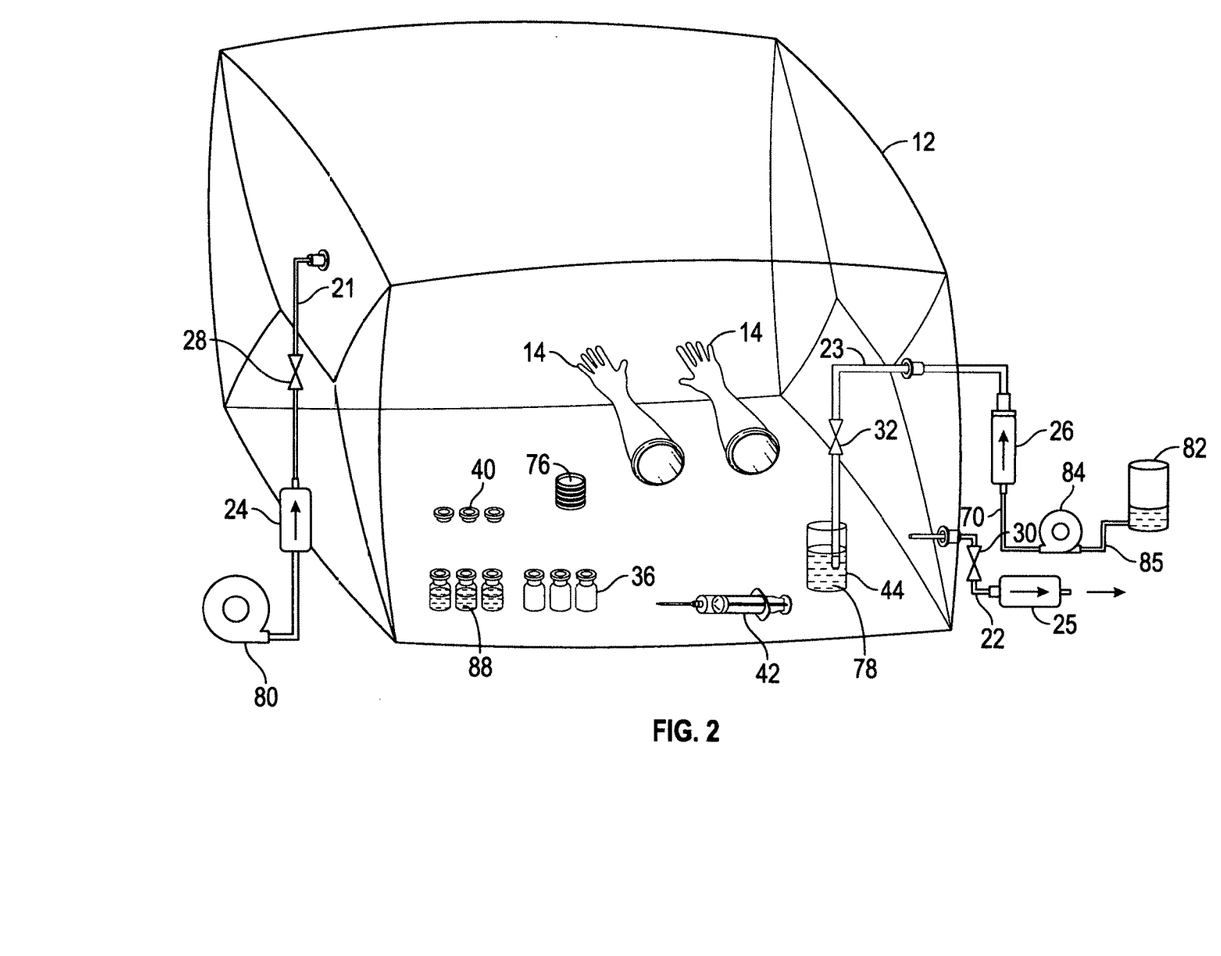
FIG. 2 shows this same embodiment of an enclosure assembly in use, with liquid solution attached to the liquid sterilizing filter, and with an air blower attached to the inlet air sterilizing filter, and also showing solution that has been filtered into the enclosure, a syringe for filling bottles, and an assortment of filled and unfilled bottles.

REFERENCE NUMBERS 12 enclosure
14 gloves
21 flexible tubing
22 flexible tubing
23 flexible tubing
24 connecting device, specifically an air inlet filter
25 connecting device, specifically an air outlet filter
26 connecting device, specifically a liquid sterilizing filter
28 pinch valve
30 pinch valve
32 pinch valve
34 bag for vials or stoppers
36 vials or bottles
38 bag for closures
40 stoppers or caps
42 means for filling product into vials or bottles
44 beaker
46 fused seam of enclosure
50 means of attaching glove to enclosure surface
52 elastomeric band
58 means of sealing flexible tubing to enclosure at point of penetration
64 means of sealing flexible tubing to enclosure at point of penetration
68 means of sealing flexible tubing to enclosure at point of penetration
70 flexible tubing at solution filter inlet
76 microbiological growth media, means for monitoring sterility of internal chamber air and surfaces
78 filtered sterile solution
80 air pump, means for inflating the enclosure or for purifying the air quality within the enclosure
82 vessel
84 pump, means for transferring product into the enclosure
85 transfer tubing
88 filled vials or bottles with closures attached
90 sterile vessel containing pre-sterilized product
92 connecting device, specifically one half of a sterile connector pair
94 half of a sterile connector pair
96 sterile tubing DETAILED DESCRIPTION—FIGS. 1 and 2—FIRST EMBODIMENT FIGS. 1-2 show one embodiment of the invention, specifically a flexible, inflatable enclosure or chamber with attachments and associated components. FIG. 1 shows the apparatus in inflated configuration, as it would look when filled with air after initial assembly. FIG. 2 shows this same embodiment as it would look in use during a sterile filling operation.

Structure of First Embodiment Shown in FIG. 1

FIG. 1 shows a flexible, inflatable enclosure (12). Gloves (14) are attached to the enclosure and protrude into the enclosed space. Lengths of flexible tubing or hoses (21, 22, 23) penetrate the enclosure at three locations and provide air or fluid pathways into the enclosure. Connecting devices, such as filters or sterile connectors (24, 25, 26) are attached to the tubing on the outside of the enclosure. Pinch valves (28, 30, 32) are attached to the lengths of tubing at various locations inside and outside of the enclosure. Bags (34) of empty bottles, vials, or other types of containers (36) designed to hold sterile product are located within the enclosure. Bags (38) of closures (40), such as bottle caps or vial stoppers, are also located within the enclosure. Syringe(s) (42) and beaker(s) (44) are also located on the inside of the enclosure.

The enclosure of this embodiment is made of flexible, transparent polyvinyl chloride film, however other types of inflatable material, such as polyethylene, polypropylene or nylon may also be used, provided that the materials are transparent and are known to be physically compatible with exposure to gamma irradiation or ethylene oxide gas. The enclosure in this embodiment is formed by cutting sheets of polyvinyl chloride film to appropriate dimensions and by then using a heat sealer to melt and fuse the edges of the film at the seams (46). Alternate methods of sealing the edges of the film, such as application of adhesives, may be used to seal the edges of the enclosure material. In this embodiment, the enclosure is formed and sealed into the shape of a rectangular cuboid, however other shapes for the enclosure may be utilized, such a spherical, triangular, or pillow shapes. The edges are required to be sealed in a manner that will prevent leakage of air through the seals, and therefore sufficient to prevent ingress of microorganisms into the inside of the enclosure, once sterilized.

In this embodiment two long-sleeved gloves (14) are attached to the surface of the enclosure and protrude into the inside space of the enclosure. The gloves of this embodiment are made of polyethylene, however other materials such as nylon, latex, neoprene or nitrile may be used. The gloves may be attached to the enclosure using any of a number of designs of flanges or fittings, well known to those who have used or manufactured glove-bags or glove-boxes. In this embodiment the gloves are attached with elastomeric bands (52) to rigid plastic flanges (50) which are sealed with silicon sealant to the surface of the enclosure. The seals between the gloves and the enclosure are required to be airtight, so that they will not leak when the enclosure is inflated with air.

In this embodiment, one length of flexible tubing, for the purpose of air ingress (21), is connected to and penetrates the enclosure on one of the sides of the enclosure. A short length of the tubing penetrates to the inside of the enclosure. A pharmaceutical grade air-sterilizing filter (24) for inlet air, is attached to the other end of the tubing, located outside of the enclosure. The filter is oriented for the ingress of air from the outside of the enclosure, through the filter, to the inside of the enclosure. In this embodiment the tubing is sealed to the surface of the enclosure at the point of penetration with a rigid plastic airtight compression fitting (58), such as the type typically used for watertight electrical cord connections. Alternate methods, such as the use of silicone sealant or heat sealed flanges, may also be used for sealing the tubing to the enclosure. The seal between the tubing and the surface of the enclosure is required to be airtight to prevent leakage when the enclosure is inflated. A pinch clamp (28) is attached to the tubing between the air inlet filter (24) and the point where the tubing enters the enclosure (58).

In this embodiment, another length of flexible tubing (22), for the purpose of air egress, is connected to and penetrates the enclosure on the opposite side of the enclosure from the air ingress tubing (21) mentioned above. A short length of the tubing penetrates to the inside of the enclosure. A pharmaceutical grade air-sterilizing filter (25) is attached to the other end of the tubing, located outside of the enclosure. The filter is oriented for the egress of air from the inside of the enclosure, through the filter, to the outside of the enclosure. The tubing is sealed to the surface of the enclosure at the point of penetration with a rigid plastic airtight compression fitting (64) of the type described above. A pinch clamp, or tube clamp (30) is attached to the tubing between the compression fitting (64) and the air outlet filter (25).

In this embodiment, another length of flexible tubing (23), for the purpose of transfer of sterile product into the enclosure, is connected to and penetrates the enclosure. A length of this product transfer tubing penetrates to the interior of the enclosure. This length of tubing should be at least long enough to reach approximately one-fourth of the distance across the interior of the enclosure. In this embodiment, a connecting device (26) is attached to the end of the tubing on the outside of the enclosure. In this instance the connecting device is a sterilizing filter. The filter is oriented so that the liquid will flow from the outside of the enclosure, through the filter and tubing to the inside of the enclosure. The tubing is sealed to the surface of the enclosure at the point of penetration with a rigid plastic airtight compression fitting (68) of the type described above. Another short length of flexible tubing (70) is attached to the upstream side of the liquid sterilizing filter. A pinch clamp (32) is attached to the length of tubing on the inside of the enclosure. If a product that has already been sterilized is to be transferred into the enclosure for filling, a sterile connector could be used as the connecting device (26), instead of a sterile filter. The sterile connector could be of the type made by various pharmaceutical equipment companies in which the sterile connector comes as two compatible halves. In this instance one half would be connected to the enclosure tubing (23) as a connecting device (26) and the other half (26) would be connected to the supply line (70) coming from the sterile product vessel (not shown).

Bags (34) of containers (36), such as bottles, vials IV-bags, or empty barrels for pre-filled syringes, are placed inside of the enclosure during initial assembly, before sealing the enclosure. Bags (38) of closures (40), such as caps, lids or stoppers, intended for sealing the aforementioned containers are also placed inside of the enclosure during initial assembly. Syringes (42) or other tools or devices for performing manual filling procedures are placed inside of the enclosure space during assembly. While syringes are shown for this embodiment, other manual filling tools, such as pipettes, scoops or spatulas (not shown) may also be used. Plastic beaker(s) (44), or similar holding vessels that can be used to temporarily hold sterile product that has been filtered into the enclosure, are also placed into the enclosure space during assembly. All of these components that are included inside of the enclosure during assembly prior to sealing the enclosure may be grouped and organized inside of bags. Microbiological growth media (76), such as RODAC touch plates, air-settling plates or test tubes of broth with swabs, may also be placed into the enclosure, for eventual microbiological monitoring of the sterile environment.

All of the materials used in the assembled embodiment of FIG. 1 have been selected based on their tolerance to exposure to gamma irradiation. Gamma radiation sterilization processes frequently expose materials to radiation doses in the range of 25 to 50 kilogray, and therefore it is desirable for the materials selected to be able to maintain their physical and functional integrity after gamma radiation doses of at least 25 kilogray, and preferably 50 kilogray. The flexible tubing included in this embodiment is pharmaceutical grade silicon tubing, however other types of pharmaceutical grade tubing may be used.

The size of this embodiment may be variable, however it is critical for this embodiment that the enclosure be portable and that the size is such that it can be deflated, folded and packed into a standard shipping box (not shown) that can be shipped to an irradiation sterilization facility and that the box is of a size that can meet the size and weight constraints of a radiation sterilization facility Structure of First Embodiment Shown in FIG. 2

FIG. 2 shows the first embodiment as it may appear after it has been sterilized and inflated, and while it is being used to fill sterile product (78). The enclosure (12) would be sitting on a table or bench (not shown), and a human operator (not shown) would be sitting or standing at the bench with hands inserted into the gloves (14) and would be performing manipulations inside of the enclosure. Another human operator (not shown) can be imagined to perform manipulations, such as of pumps and pinch clamps, outside of the enclosure.

FIG. 2 includes various pieces of equipment, supplied by the customer or end-user, which are not included in the scope of the invention, but which are used to support the sterile filling operation. Specifically, these include an air blower (80), used to inflate the enclosure, an external product holding vessel (82), and a pump (84) for transferring liquid product from the external holding vessel, through the liquid-sterilizing filter (26) and into the enclosure. Any number of types of air blowers, holding vessels and liquid pumps may be used, provided that they meet the standards normally applied for pharmaceutical products.

Operation of the First Embodiment

For operation of the first embodiment, reference is made to FIG. 2. After the first embodiment described above is assembled, as shown in FIG. 1, it is inflated and tested for leaks. Leaks may be detected by a number of well known methods, including soap bubble tests, audible detection, or helium detection. Once the assembly has been verified not to have any leaks, it is then deflated, folded, packaged and shipped for sterilization. Alternatively, following leak testing and prior to shipment for sterilization, the chamber may be flushed with sterile filtered air in order to reduce the levels of bioburden and particulate matter within the chamber. Sterilization is achieved through application of an appropriate gamma irradiation dose. The appropriate gamma irradiation dose may depend on product design, density, microbial bioburden and other factors. For many devices of similar size or density a dose of 25 kilogray is found to be satisfactory for sterilization. While sterilization by gamma irradiation is preferred, it is also possible and acceptable to sterilize the entire enclosure assembly using ethylene oxide gas. This is accomplished by placing the enclosure assembly into the chamber of an ethylene oxide gas sterilizer, and exposing the enclosure assembly to a validated ethylene oxide gas sterilization cycle, using procedures well known in the pharmaceutical and medical device industries.

Following sterilization, the sterile enclosure may be shipped to the end user, for the purpose of filling sterile product. To operate this embodiment of the invention, the enclosure assembly is first unpacked and placed onto a table or bench (not shown). The enclosure taught here is inflated with air, however nitrogen or an inert gas such as argon could also be used when applied with appropriate safety precautions. The air is blown into the enclosure through the air inlet filter (24) using an air blower (80). If desired, a compressed gas cylinder (not shown) could be used in lieu of an air blower to inflate the enclosure. To inflate the enclosure, the inlet air hose pinch valve (28) is opened and the other two pinch valves (30) and (32) are closed.

Once the enclosure is approximately 80% inflated, the outlet air hose clamp (30) is opened, so that a steady inlet and outlet flow can be achieved. This flow of air washes the insides of the enclosure and over a period of time, such as 30 minutes in one example, so that the inside of the enclosure will achieve a sufficiently low particulate count, as may be required for some sterile solutions. After the appropriate amount of air-wash time, the air blower is turned off, and the inlet and outlet air hose clamps are closed, leaving the enclosure in an inflated condition.

For this embodiment, the sterile product to be filled would be a liquid solution that is capable of being sterilized by filtration. The solution is held in a vessel (82), such as a beaker, a small tank, an I.V. Bag, or a bioprocessing bag. Hand are inserted into the gloves (14) and the solution-line pinch valve (32) is opened. The solution is delivered through a length of transfer tubing (85) to a pumping device (84) which is attached with tubing (70) to the connecting device (26), in this case a liquid sterilizing filter. The pumping device pumps the solution through the liquid sterilizing filter, rendering the solution sterile. From the sterilizing filter the sterile solution flows through the flexible tubing (23) and into a beaker (44), which has been sterilized during the previously described gamma radiation sterilization of the entire enclosure assembly. After a sufficient quantity of the liquid has been sterile filtered into the enclosure, pumping is discontinued and the pinch-clamp (32) on the transfer tubing is closed, to prevent additional flow. The type of pumping device used could be a hand pump, a peristaltic pump, a centrifugal pump, or other, as appropriate. It is also recognized that in some instances the product vessel (82) could be elevated and gravity alone could provide sufficient force to transfer the solution through the sterilizing filter and into the sterile enclosure.

Manual filling operations are performed inside of the sterile enclosure (12) by insertion of the operator's hands and forearms into the gloves (14) and by then manipulating various components within the sterile enclosure. The gloves act as a barrier between the human operator and the inside of the sterile enclosure. The sterile liquid (78) may now be filled into each of the sterile bottles (36) that had been sterilized inside of the enclosure during gamma radiation sterilization of the entire enclosure assembly. Filling is performed by use of a manual syringe (42), using the gloved hands to operate the syringe. Sterile solution is drawn into the syringe and a measured volume is then dispensed into the bottles. Other means of filling product into the bottles, such as use of a peristaltic pump or use of a pipette mechanism may also be used. This filling step may be repeated until a sufficient number of bottles have been filled. The appropriate caps (40) also sterilized inside the enclosure during gamma irradiation of the entire assembly are then placed onto the bottles. As mentioned previously, the containers to be filled with sterile product could be bottles, vials, IV-bags, the barrels of pre-filled syringes, or other suitable containers.

Once a sufficient quantity of filled bottles (88) have been capped, environmental monitoring of the interior of the enclosure may optionally be performed. If sterile microbiological monitoring touch plates, also known as RODAC plates (76), have been included inside of the enclosure during enclosure assembly, these RODAC plates may be opened and used to touch various surfaces inside of the enclosure. The RODAC plates are then closed, removed from the enclosure, and incubated using standard microbiological procedures. The absence of microorganism colonies on the plates following incubation may provide an indicator that the sterility of the enclosure was not compromised. It is also understood that other means of microbiological monitoring could be employed, such as the inclusion and use of air-settling plates or the inclusion and use of swabs and broth media. Following filling and environmental monitoring, the vinyl enclosure may be cut open and the bottles (88) containing the sterile product may be removed. The air filters (24, 25) and liquid filter (26) may be tested for integrity per industry standard procedures to demonstrate that they have maintained integrity, and therefore their ability to sterilize air or liquids respectively, during use.

Figure 3:
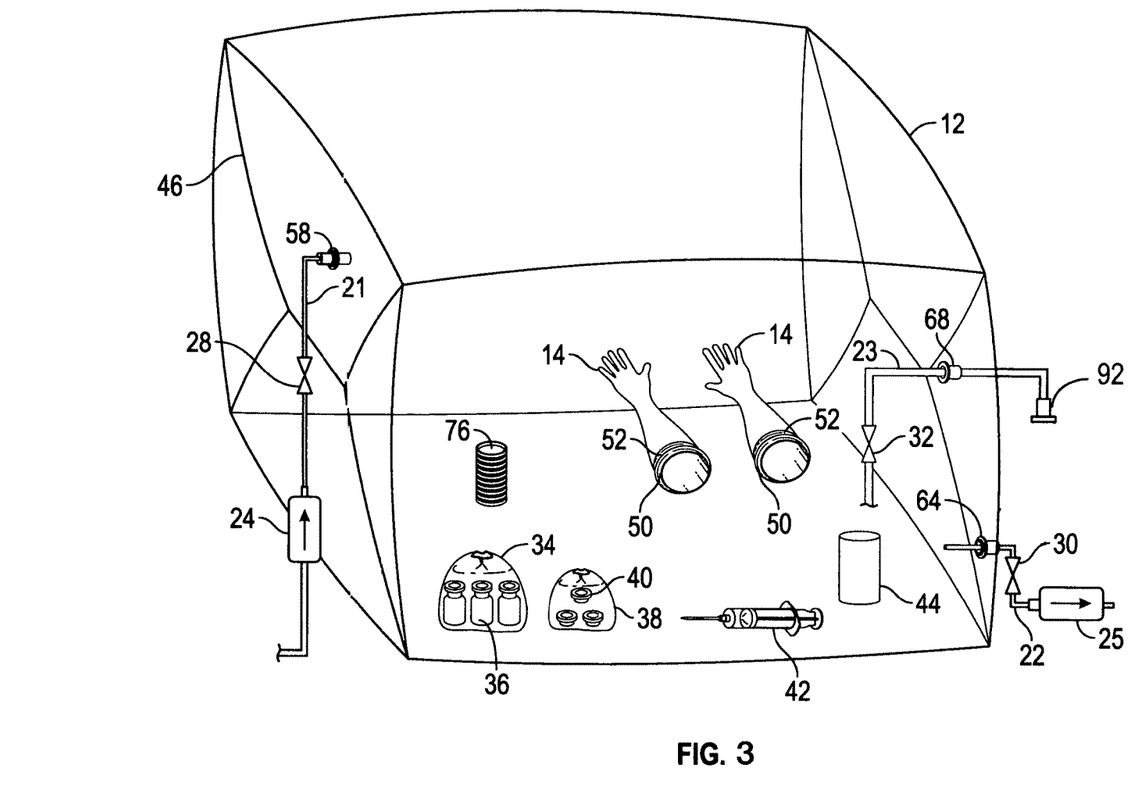
FIG. 3 shows a second embodiment of the invention with a sterile connector attached to the transfer tubing, rather than a sterilizing filter.
Figure 4:
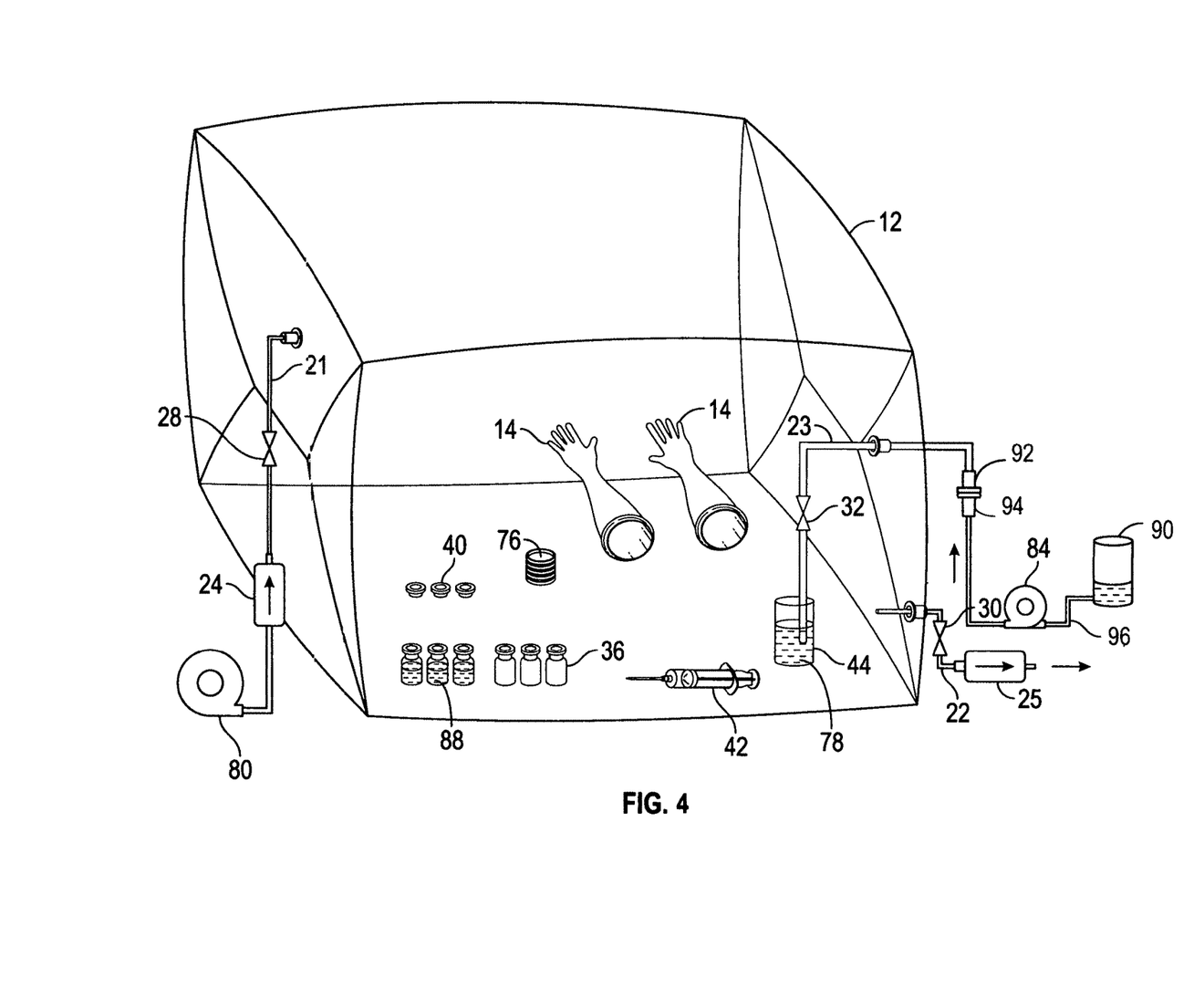
FIG. 4 shows the second embodiment in use, with sterile product being transferred into the enclosure via sterile tubing, which is attached to the enclosure tubing with a sterile connector instead of with a sterilizing filter.

DETAILED DESCRIPTION—FIGS. 3 AND 4—SECOND EMBODIMENT

FIGS. 3-4 show a second embodiment of the invention in which a sterile connector is used for the connection of the enclosure to a sterile product line. FIG. 3 shows this second embodiment of the apparatus in inflated configuration, as it would look when filled with air after initial assembly. FIG. 4 shows this second embodiment as it would look in use during a sterile filling operation.

Structure of Second Embodiment Shown in FIG. 3

FIG. 3 shows a second embodiment of the enclosure and associated parts. The components are nearly the same as the first embodiment presented in FIG. 1, with the exception that a sterile connector (92), instead of a sterilizing filter, serves as the connecting device at the distal end of the flexible supply tubing (23). The sterile connector could be of the type made by various pharmaceutical equipment companies in which the sterile connector comes as two compatible, or mating, halves, designed to enable a sterile connection when the two halves are joined and a septum between the two halves is removed. In this instance one half would be connected to the enclosure tubing (23) as a connecting device (92) and the other half (not shown) would be connected to a sterile supply line coming from the sterile product vessel (not shown).

Structure of Second Embodiment Shown in FIG. 4

FIG. 4 shows the second embodiment as it may appear after it has been sterilized and inflated, and while it is being used to fill sterile product (78). The figure shows the sterile connector (92) of enclosure assembly connected to a mating sterile connector (94), which is attached to an already sterilized vessel of sterile product (90) via an associated sterile supply line (96). This embodiment enables the sterile transfer of an already sterilized product, such as a sterile suspension, which cannot be filtered.

Operation of the Second Embodiment

The sterile filling operation for this second embodiment shown in FIGS. 3-4 is nearly the same as the operation described above for the first embodiment, with the exception that the product is already pre-sterilized in a sterile vessel (90) and is transferred into the enclosure via tubing lengths, which are attached with sterile connectors (92 and 94).

While the descriptions above contains many specifics, these should not be construed as limiting the scope of the embodiment. For example, the enclosure could have other shapes, such as pyramidal, spherical, or other; the enclosure could be made of a rigid material, not requiring inflation; the enclosure could be made of varying sizes, provided that the size fits within the dimensional requirements of gamma irradiation sterilization facilities, etc.

EXPERIMENTAL EXAMPLES AND RESULTS

Example #1

An enclosure constructed according to FIG. 1, above, was tested for particles per cubic foot after blowing air through the chamber with a pump operating at approximately 1 cubic feet per minute. The particle counts were measured at the air outlet tubing using an electronic particle counter. The results are provided in the table below. The results show that the flow of filtered air through the isolator will, over time, reduce the counts of particles of a size 0.5 micrometers or larger to levels below 100 per cubic foot, which is a recognized standard for operation of closed system isolators.

| Time of airwash (minutes) | Number of Particles ≥0.5 micons per cubic foot |
| --- | --- |
| 0 | 4000 (approximate) |
| 5 | 2000 (approximate) |
| 10 | 460 |
| 15 | 212 |
| 25 | 59 |
| 35 | 16 |

Example #2

An apparatus fabricated according to the first embodiment described above was manufactured, assembled, deflated, and sterilized with 25 kGy gamma radiation. After sterilization, the enclosure was placed in an uncontrolled warehouse-like environment and was inflated by blowing air through the inlet air-sterilizing filter. A solution of trypticase soy broth (TSB) was prepared and filtered through the liquid sterilizing filter. Following filtration the sterile liquid growth media was collected in the sterile plastic receptacle, which had been in-situ sterilized within the enclosure during enclosure gamma sterilization. The TSB Media was then filled into sterile vials and bottles within the enclosure, and stoppers or caps were then placed onto the vials and bottles. Four containers (two glass vials and two plastic bottles) containing media were purposefully exposed to microorganisms as positive controls. The media filled containers and the positive controls were then incubated at approximately 84° F. for 14 days. After 14 days, each of the 13 glass test vials was clear, and each of the 79 plastic bottles was clear, all indicating no bacterial growth, and therefore indicating sterility. Each of the four positive controls was visibly cloudy, indicating that the media in the test containers was capable of supporting growth, if contaminated. The results are tabulated below:

|  | Glass vials | Plastic eye-drop bottles |
| --- | --- | --- |
| Number filled with media | 13 | 79 |
| Visual results after 7 days incubation | 13 vials clear (no growth) | 79 bottles clear (no growth) |
| Visual results after 14 days incubation | 13 vials clear (no growth) | 79 bottles clear (no growth) |
| Positive controls after 2 days incubation | Both vials cloudy | Both vials cloudy |

Example #3

An apparatus fabricated according to the first embodiment described above was manufactured, assembled and sterilized with 25 kGy gamma radiation. The sterile package was stored for approximately two years in an uncontrolled warehouse-like environment. Following two years of storage, the enclosure was unpacked from the corrugated cardboard shipping box and, in an uncontrolled warehouse-like environment, was inflated by blowing air through the inlet air-sterilizing filter. A solution of TSB was prepared and filtered through the liquid sterilizing filter. Following filtration the sterile liquid growth media was collected in the sterile plastic receptacle, which had been in-situ sterilized within the enclosure during enclosure gamma sterilization. The TSB Media was then filled into sterile vials and bottles within the enclosure, and stoppers or caps were then placed onto the vials/bottles. Three containers (one glass vial and two plastic bottles) containing media were purposefully exposed to microorganisms as positive controls. The media filled containers and the positive controls were then incubated at approximately 80° F. for 14 days. After 14 days, each of the 5 glass test vials was clear, and each of the 45 plastic bottles was clear, all indicating no bacterial growth, and therefore indicating sterility. Each of the three positive controls was visibly cloudy, indicating that the media in the test containers was capable of supporting growth, if contaminated. The results are tabulated below:

|  | Glass vials | Plastic eye-drop bottles |
| --- | --- | --- |
| Number filled with media | 5 | 45 |
| Visual results after 7 days incubation | 5 vials clear (no growth) | 45 bottles clear (no growth) |
| Visual results after 14 days incubation | 5 vials clear (no growth) | 45 bottles clear (no growth) |
| Positive controls after 2 days incubation | visibly cloudy | visibly cloudy |

In addition, following the fill described in Example #3, an additional sterility challenge was performed by puncturing the inflated chamber wall with four small pinholes and exposing a portion of media in an open tray inside of the inflated enclosure for seven (7) days. This media remained clear during the entire 7-day period, indicating the absence of microorganisms. Following the 7-day holding period, which was at an average temperature of approximately 80° F., a portion of the media in the open tray was transferred into a second container and lids were placed onto both containers of media. These manipulations were performed using the integral glove-ports described above. The isolator enclosure was then opened and both of the media containers were removed. One of the containers remained closed. The second container was intentionally contaminated by removal of the lid for several minutes, and then replacement of it. The two trays of media were incubated for two days at 80° F. Surprisingly, the unopened tray remained clear (sterile) and the positive control tray became cloudy. This experiment demonstrated that the interior of the inflated portable isolator enclosure remained sterile for at least one week following initial inflation and use, even though the inflated chamber had been punctured with several pinholes. The significance of this surprising observation is that small accidental holes made in the chamber during construction or use would not appear to compromise the sterility of the filling operation, provided that the air pressure in the inflated chamber remained higher than the external air pressure, thus preventing ingress of microorganisms from the outside environment.

Conclusion, Ramifications and Scope

The invention taught here solves the problem of filling a small number of vials or bottles of sterile product, without requiring dedicated space or expensive equipment or facilities. By use of the portable enclosure taught here, and by sterilizing the enclosure along with all necessary attachments and enclosed vials in their entirety using gamma radiation or ethylene oxide gas, it becomes possible to achieve high levels of sterility assurance without the use of expensive equipment or dedicated infrastructure normally associated with aseptic filling operations.

Further, the apparatus and the method of use taught here, enables the achievement of higher sterility assurance levels than are normally achieved with conventional aseptic cleanrooms, or with laminar flow workbenches, even when used in uncontrolled environments, as may be found in remote or undeveloped locations.

In addition, the apparatus taught here provides the advantage of being capable of being shipped to off-site facilities for sterilization, and subsequently being shipped to distant locations, once sterilized, where it may be used for the filling of sterile product with minimal preparation by the user, and without the need for subsequent sterilization steps, other than the sterilization of air or liquids as they pass through the filters integral to the enclosure.

We claim:

1. A non-sterile assembly adapted to be sterilized and used for filling sterile product, comprising:
   a. a deflated sealed enclosure consisting of a perimeter surface and a non-sterile inside space,
   b. at least one empty container and a respective lid or closure, located in the non-sterile inside space of the sealed enclosure,
   c. a plurality of gloves contiguous with the perimeter surface of the enclosure and protruding as an extension of the perimeter surface of the enclosure towards the inside space of the enclosure,
   d. a plurality of lengths of tubing, the lengths of tubing configured to transfer sterile material into the inside space of the enclosure, penetrating from the outside of the enclosure to the inside space of the enclosure, said lengths of tubing attached and sealed to the perimeter surface of the enclosure at respective points of penetration,
   e. a sterilizing filter attached to a distal end of each respective length of said tubing located on the outside of the enclosure, said sterilizing filters configured to maintain sterility of respective internal lumen of the tubing following sterilization and for sterile connection of said lengths of tubing to product supply lines and air supply lines external to the assembly,
   f. at least one filling device located in the inside space of the sealed enclosure, said at least one filling device configured to transfer sterile product into said at least one container within the inside space of the enclosure,
   g. microbiological growth media plates or broth tubes, included in the inside space, configured to test the microbiological quality of the inside space of the sealed enclosure,
   h. whereby the deflated sealed enclosure, with the at least one empty container and respective lid or closure, the at least one filling device, and the microbiological growth media plates or broth tubes located in the non-sterile inside space, is configured to be folded and packed into a shipping box and is configured to be inflated after shipping,
   i. wherein the non-sterile assembly is adapted to be sterilized using gamma irradiation prior to reaching an end user.

2. The assembly of claim 1, wherein the non-sterile assembly is configured to be sterilized as a completely assembled unit using gamma irradiation as the sterilization method, and said sterilization occurring in one sterilization step.

3. The assembly of claim 1, wherein the enclosure is made of flexible material, thus rendering the enclosure inflatable.

4. The assembly of claim 1, wherein said at least one filling device comprises syringes, pipettes, scoops or spatulas, and said at least one filling device is included inside of the enclosure prior to sterilization of the assembly.

5. The assembly of claim 1, wherein the at least one container comprises vials, bottles, intravenous solution bags, or empty pre-filled syringe barrels, and said at least one container is included inside of the enclosure prior to sterilization of the assembly.

6. The assembly of claim 1, wherein the sterilizing filters comprise a liquid-sterilizing filter and associated filter-housing.

7. The assembly of claim 1, wherein the assembly can be rendered to a size that can be sterilized using standard procedures at gamma irradiation sterilization facilities.

8. The assembly of claim 1, wherein the sterilizing filters comprise an air sterilizing filter and associated filter-housing, said filter intended for sterilizing air or other gases.

9. The assembly of claim 1, wherein all of the materials of use are compatible with gamma sterilization at a dose of at least 25 kGy.

10. The assembly of claim 1, wherein after sterilization, sterility of the interior space and surfaces is configured to be maintained without the need for positive pressure and without the need for the continuous flow of sterile air through the enclosure.

11. The assembly of claim 1, wherein the assembly is configured to be shipped to an end user in sterile condition, and wherein an end user does not need to perform any additional sterilization of the apparatus, and wherein an end user is not required to perform any aseptic or sterile connections in order to use the assembly.

12. The assembly of claim 1, wherein the assembly is configured to be stored in sterile condition for up to two years prior to use.

13. The assembly of claim 1, wherein an end user does not need to separately sterilize, or transfer into the enclosure, the containers to be filled.

14. A sterile enclosure assembly used for filling sterile product, comprising:
- a deflated enclosure having a surface and configured to be inflated,
- at least two flexible hoses which penetrate and attach to the enclosure,
- at least one liquid-sterilizing filter and at least one air-sterilizing filter connected to respective external distal ends of said at least two hoses,
- gloves protruding into said enclosure, said gloves contiguous with and integral to the surface of said enclosure,
- bottles or vials or other containers and associated closures located inside of said deflated enclosure prior to, during, and after sterilization,
- tools configured to manually fill said bottles or vials or other containers located inside of said deflated enclosure prior to, during, and after sterilization,
- microbiological growth media with associated media plates or broth tubes included in the deflated enclosure prior to, during, and after enclosure sterilization,
- valves respectively attached to said at least two hoses for sealing or opening said at least two hoses,
- wherein said enclosure assembly is sealed to prevent ingress of microorganisms to the inside of said enclosure assembly, and
- wherein said enclosure assembly is sterilized in its entirety as an assembled unit, using gamma irradiation,
- wherein said sterile enclosure assembly is configured to be folded and packed into a shipping box,
- wherein said sterile enclosure assembly is configured to perform a sterile fill within said enclosure without additional sterilization steps subsequent to shipping.

* * * * *